United States Patent [19]

Bellati

[11] Patent Number: 4,669,455

[45] Date of Patent: Jun. 2, 1987

[54] PNEUMATIC TRACTOR FOR THE TREATMENT OF DEFORMITIES OF THE SPINE

[75] Inventor: Patrizia Bellati, La Spezia, Italy

[73] Assignee: Co.Pro.San. S.r.l., Italy

[21] Appl. No.: 698,352

[22] Filed: Feb. 5, 1985

[30] Foreign Application Priority Data

Feb. 6, 1984 [IT] Italy .................. 11538/84[U]

[51] Int. Cl.$^4$ ............................................. A61F 5/02
[52] U.S. Cl. .................................... 128/78; 128/69; 128/118; 5/449
[58] Field of Search ................. 128/59, 60, 61, 67, 128/68, 69, DIG. 20, 78, 95, 106, 118; 5/432, 433, 436, 441, 449, 453, 456, 446

[56] References Cited

U.S. PATENT DOCUMENTS

| 1,228,783 | 6/1917 | Kerivan | 5/449 |
| 1,755,205 | 4/1930 | Christensen | 5/449 |
| 2,521,530 | 9/1950 | McGuffage | 5/449 |
| 2,967,524 | 1/1961 | Christensen | 128/69 |
| 4,135,503 | 1/1979 | Romano | 128/118 |

FOREIGN PATENT DOCUMENTS

| 2657619 | 6/1978 | Fed. Rep. of Germany | 128/69 |
| 1015989 | 10/1952 | France | 128/69 |

*Primary Examiner*—John J. Wilson
*Attorney, Agent, or Firm*—McGlew and Tuttle

[57] ABSTRACT

A tractor for the treatment of deformities of the spine comprises a plate of rigid material such as plastic having a raised peripheral rib extending outwardly from the plate in the form of an elongated figure 8 which encloses a substantially cylindrical end portion at each end interconnected by a central connecting portion space which is covered by a flexible elastic membrane so as to form two airtight chamber portions at each end and a narrow central connecting portion which communicates therebetween. The end portions may be inflated outwardly with the use of a portable hand pump or bellows connected thereto and the device is adapted to be engaged with a brace applied around the person's body.

5 Claims, 3 Drawing Figures

PNEUMATIC TRACTOR FOR THE TREATMENT OF DEFORMITIES OF THE SPINE

FIELD AND BACKGROUND OF THE INVENTION

The present invention relates to body conditioning devices and in particular to a new and useful pneumatic tractor for the treatment of deformities of the spine.

It is known that the spine is not straight, but has a number of curvatures, very pronounced and constant along the sagittal plane and very minor and inconstant along the frontal plane. Of the former, there are four, each corresponding to a portion of the spine, namely the cervical and lumbar curvatures, convex toward the front, and the dorsal and sacral curvatures, convex toward the back.

Deviations of the spine cause various pathological conditions, such as hunchback, lumbar hyperlordosis, scoliosis, etc.

It is known that heretofore such deformities of the spine have been corrected, depending on the gravity, by orthopedic corsets and bodices, plaster apparatus, surgical vertebral fixation such as arthrodesis. Apart from the plaster apparatus and surgical interventions, which are reserved for the most serious cases, the orthopedic corsets and bodices known today use plates or splints of metal and/or rigid plastic, but such guards are not very effective and moreover cause the patient serious physical and psychological discomfort. The present invention sets itself the task to eliminate the inconveniences by proposing a device capable of correcting—in a bloodless manner—the deviations of the spine.

SUMMARY OF THE INVENTION

This result has been achieved according to the invention by adopting the idea of causing a longitudinal traction of the deformed spine zone, until its proper curvature is restored, by using the diverging vertical thrust of two elastic bladders, spaced but joined by a small tube, and inflated with air and kept in place by an ordinary cloth corset.

Advantages of the present invention are that the traction is localizable and adjustable as to intensity; that it is possible to obtain stable and permanent mofifications of the various deformities of the spine; that the device is easy to manufacture, simple and convenient to apply, and is tolerated well even after long periods.

Accordingly, it is an object of the invention to provide an improved tractor which includes a plate member which has inflatable spaced apart portions which are inflatable to bear at spaced locations against a persons spinal zone for the purpose of restoring proper curvature thereto.

A further object of the invention is to provide a device for applying pressure to areas of the body which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
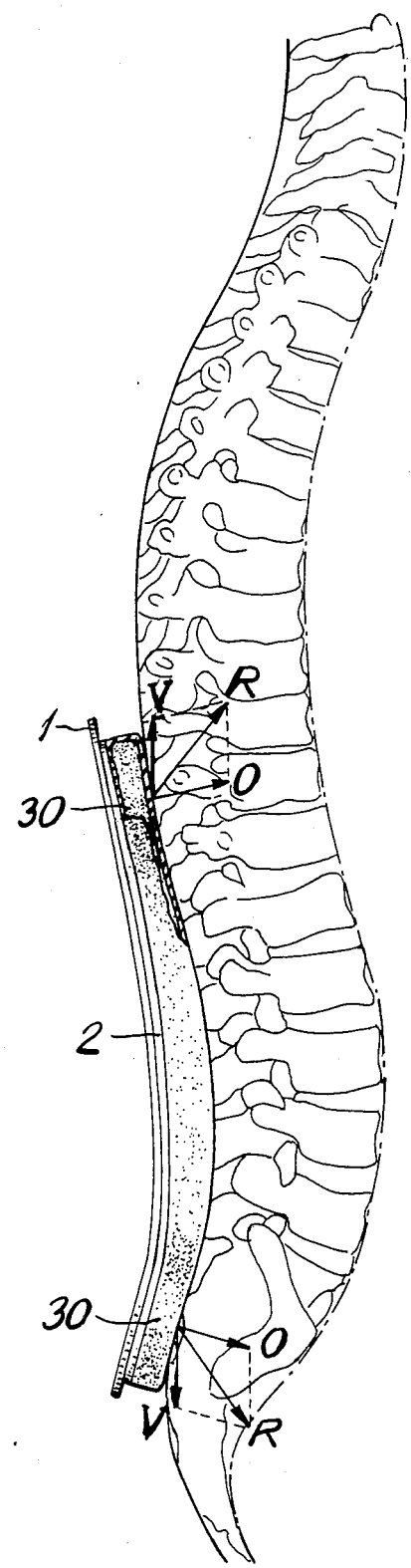
FIG. 1 is a schematical sectional view in vertical section of a pneumatic tractor according to the invention in a possible arrangement of use.
Figure 2:
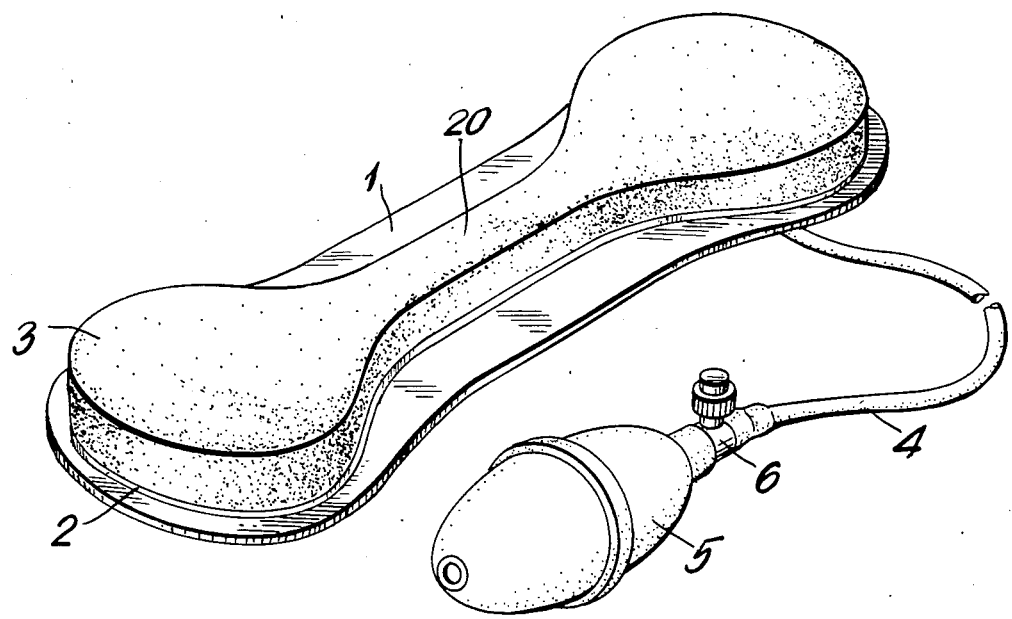
FIG. 2 is a top perspective view of the tractor of FIG. 1 in its inactive state.
Figure 3:
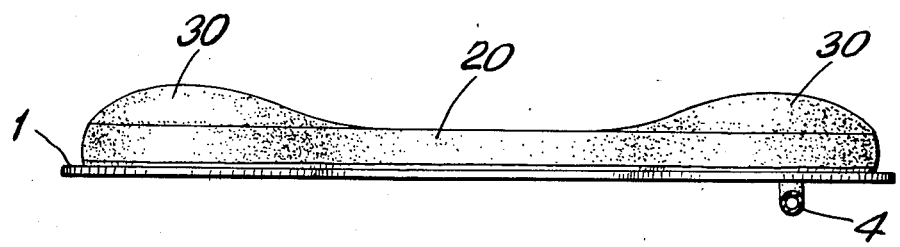
FIG. 3 is the side elevational view of the tractor of FIG. 1, inflated but not in use.

Referring to the drawings in particular, the invention embodied therein comprises a tractor for the treatment of deformities of the spine and which is adapted to be used in conjunction with a back brace or corset and which comprises a plate 1 of a rigid plastic material having a rib which extends outwardly from one side of the plate and has the form of an elongated figure 8 and encloses substantially cylindrical end portions with a central connecting portion extending between the end portions, a flexible and elastic membrane 3 which covers the space and defines with the rib 2 and the plate 1 to end portion airtight chambers 3, 30 which are interconnected by a narrow central passage connecting portion 20 which communicates between the end portion airtight chambers 30.

A pneumatic tractor for the treatment of deformities of the spine according to the invention includes, a plate 1, from one side of which a rib 2 emerges in the form of an elongated figure 8 and closed at the top by a flexible and elastic membrane 3 which with the rib 2 and the plate 1 defines two airtight chambers 30 and a central passage 20 which lets the two chambers 30 communicate. One of the two chambers 30 is provided with an air inlet, preferably passing through the plate 1, and provided with a flange for the attachment of a rubber tube 4, which in turn is connected to a hand pump 5 with a holding and deflating valve.

Beforehand the tractor is placed, not inflated, inside an ordinary cloth corset, with the two chambers 30 turned toward and against the patient's back, in vertical position and with the lower chamber at the lumbosacral passage and the upper chamber at the spinal zone to be treated, and held in that position by the pulled laces of the corset.

Then, by operating the pump 5, the air chambers 30 are inflated; under the action of the air pressure, their membranes 3 rise, acquiring a good hardness, but staying substantially flat, with the cooperation of the rib 2. The increase in height or thickness of the chambers 30 occurs toward and against the wearer's back, since the plate 1 is rigid and therefore not deformable, so that a force R is exerted by each chamber 30 on the corresponding support zone. The two forces R, which are oriented differently, namely that belonging to the upper chamber 30 upward and that belonging to the lower chamber 30 downward, have the respective vertical components V, or rather parallel to the respective support surfaces, extending in opposite directions. These two forces V exert a longitudinal traction of the zone of the spinal column between the two chambers 30 of the tractor, a force which, even if the air pressure is low, is sufficient to correct irregular (improper) curvatures of the spine. It is evident that the horizontal forces 0, or rather those perpendicular to the support surfaces of the chambers, are cancelled by the counter-pressure exerted by the corset.

In practice, the design details may vary in equivalent manner as to form, dimensions, arrangement of the elements, nature of the materials employed, without going outside the scope of the idea of solution adopted and therefore remaining within the limits of the teaching given by the present patent for industrial invention.

While a specific embodiment of the invention has been shown and described in detail to illustrate the application of the principles of the invention, it will be understood that the invention may be embodied otherwise without departing from such principles.

What is claimed is:

1. A tractor for the treatment of deformities of the spine, comprising a plate of rigid material, a raised rib extending outwardly from one side of said plate and having the form of an elongated figure eight including substantially cylindrical end portions and a narrow central connecting portion space, a flexible and elastic membrane covering the space and defining with said rib and said plate two end portion airtight chambers and a narrow central passage connecting portion communicating between said end portion airtight chambers, each of the air-tight portion chambers being inflatable so that they extend outwardly from said raised rib.

2. A tractor according to claim 1, including an air intake connected to one of said chambers and passing through said plate.

3. A tractor according to claim 2, wherein said air intake is of a rigid material and forms an attachment for a rubber connecting tube.

4. A tractor according to claim 3, including a hand pump connected to a tube which is connected to said air intake, said pump having a deflating valve.

5. Process for treating deformities of the spine to provide vertically longitudinal traction, which comprises providing a tractor having a plate of rigid material, a raised rib extending outwardly from one side of said plate and having the form of an elongated figure eight including substantially cylindrical end portions and a narrow central connecting portion space, a flexible and elastic membrane covering the space and defining with said rib and said plate two end portion airtight chambers and a narrow central passage connecting portion communicating between said end portion airtight chambers, each of the airtight portion chambers being inflatable so that they extend outwardly from said raised rib, vertically longitudinally aligning the side of the plate having the inflatable chambers with the spine of the person to be treated, in the area requiring traction, and closing the tractor by a corset, and thereafter inflating the chambers to cause them to bear against the spine, whereby to provide such vertically longitudinal traction.

* * * * *